(12) United States Patent
Ozaki

(10) Patent No.: US 11,600,020 B2
(45) Date of Patent: Mar. 7, 2023

(54) BIOLOGICAL SUBSTANCE QUANTIFICATION METHOD, IMAGE PROCESSING DEVICE, PATHOLOGICAL DIAGNOSIS SUPPORT SYSTEM, AND RECORDING MEDIUM STORING COMPUTER READABLE PROGRAM

(71) Applicant: Konica Minolta, Inc., Tokyo (JP)

(72) Inventor: Yuichi Ozaki, Tokyo (JP)

(73) Assignee: Konica Minolta, Inc., Tokyo (JP)

( * ) Notice: Subject to any disclaimer, the term of this patent is extended or adjusted under 35 U.S.C. 154(b) by 267 days.

(21) Appl. No.: 16/754,801

(22) PCT Filed: Oct. 17, 2018

(86) PCT No.: PCT/JP2018/038581
§ 371 (c)(1),
(2) Date: Apr. 9, 2020

(87) PCT Pub. No.: WO2019/078230
PCT Pub. Date: Apr. 25, 2019

(65) Prior Publication Data
US 2021/0192786 A1    Jun. 24, 2021

(30) Foreign Application Priority Data
Oct. 19, 2017    (JP) .............................. JP2017-202249

(51) Int. Cl.
*G06K 9/00*    (2022.01)
*G06T 7/80*    (2017.01)
(Continued)

(52) U.S. Cl.
CPC ........... *G06T 7/80* (2017.01); *G01N 21/6428* (2013.01); *G01N 21/6456* (2013.01);
(Continued)

(58) Field of Classification Search
None
See application file for complete search history.

(56) References Cited

U.S. PATENT DOCUMENTS

| 2011/0242485 A1 | 10/2011 | Kishimoto et al. |
| 2013/0338014 A1 | 12/2013 | McDonough et al. |
| 2017/0276598 A1 | 9/2017 | Ikuyama |

FOREIGN PATENT DOCUMENTS

| EP | 3086110 | 10/2016 |
| JP | 2004157018 | 6/2004 |

(Continued)

OTHER PUBLICATIONS

Extended European Search Report issued in corresponding EP Application No. 18868433.6, dated Oct. 23, 2020.
(Continued)

*Primary Examiner* — Wei Wen Yang
(74) *Attorney, Agent, or Firm* — BakerHostetler

(57) ABSTRACT

A biological substance quantification method of quantifying an expression amount of a specific biological substance in a target sample stained by using a fluorescent dye accumulated particle bondable to the specific biological substance. The method includes: inputting a first fluorescent image obtained by image capturing of the target sample; extracting a bright spot portion from the first fluorescent image and calculating a first luminance value; and calculating a number of the fluorescent dye accumulated particle included in the bright spot portion by using the first luminance value, a second luminance value of a bright spot portion extracted from a second fluorescent image obtained by image capturing of a standard sample, and a distribution of a third luminance value of each bright spot portion in a third fluorescent image obtained by image capturing of a prepa- (Continued)

ration on which the fluorescent dye accumulated particle is dispersed without aggregating.

10 Claims, 7 Drawing Sheets

(52) U.S. Cl.
CPC ........... *G06T 7/0012* (2013.01); *G16H 50/20* (2018.01); *G01N 2021/6439* (2013.01); *G06T 2207/10064* (2013.01); *G06T 2207/30024* (2013.01)

(56) References Cited

FOREIGN PATENT DOCUMENTS

| JP | 2006-177956 A | 7/2006 | | |
|----|---------------|--------|---|---|
| JP | 2009-098151 A | 5/2009 | | |
| JP | 5593221 | 9/2014 | | |
| WO | 2012029342 | 3/2012 | | |
| WO | WO-2015163211 A * | 10/2015 | ............. | G01N 21/64 |
| WO | WO 2016/006096 A1 | 1/2016 | | |
| WO | 2016129061 | 8/2016 | | |
| WO | WO 2016/125236 A1 | 8/2016 | | |
| WO | WO-2016129061 A1 * | 8/2016 | ............. | G01N 21/64 |

OTHER PUBLICATIONS

International Search Report issued in parent PCT/JP2018/083581, dated Jan. 22, 2019.
International Patent Application No. PCT/JP2018/038581; Int'l Preliminary Report on Patentability; dated Apr. 21, 2020; 8 pages.
European Patent Application No. 18868433.6; Office Action—Article 94(3); dated May 25, 2021; 9 pages.

* cited by examiner

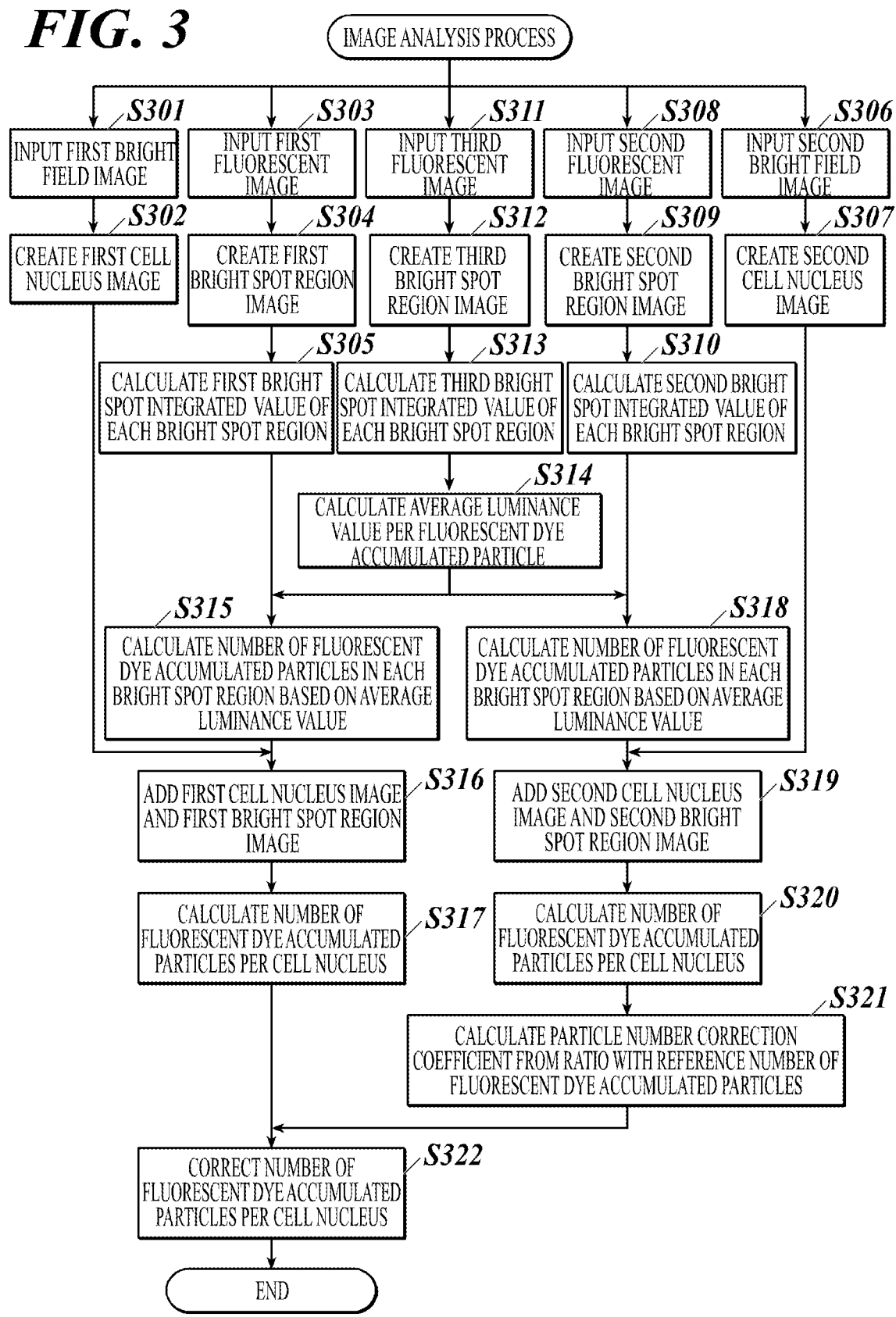

BIOLOGICAL SUBSTANCE QUANTIFICATION METHOD, IMAGE PROCESSING DEVICE, PATHOLOGICAL DIAGNOSIS SUPPORT SYSTEM, AND RECORDING MEDIUM STORING COMPUTER READABLE PROGRAM

The present U.S. Patent Application is U.S. National Phase Application under 35 U.S.C. 371 of International Application PCT/JP2018/038581 filed on Oct. 17, 2018, which claims a priority under the Paris Convention to Japanese Patent Application No. 2017-202249 filed on Oct. 19, 2017, the entire disclosures of which are incorporated herein by reference in their entireties.

TECHNICAL FIELD

The present invention relates to a biological substance quantification method, an image processing device; a pathological diagnosis support system, and a program, particularly relates to an image process used in pathological diagnosis.

BACKGROUND ART

In pathological diagnosis, quantifying the expression amount of biological substance overexpressing in a tissue slice is very important information for prognostic expectation and for determination of future treatment plan. In such quantification of biological substance, development of the method that enables accurate quantification of biological substance and extraction of region of interest has been desired for analysis of the expression amount of a specific biological substance in the region of interest that is an analysis target region set in the tissue slice.

Conventionally, there has been used a method of extracting fluorescent bright spots from a fluorescent image obtained by image capturing of a tissue sample stained with a specific protein using fluorescent dye accumulated particles, and counting the number of bright spots to perform the quantitative evaluation of biological substance. However, there may be cases where a single bright spot is seen on the fluorescent image but actually a plurality of fluorescent dye accumulated particles are accumulated. Thus, accurate quantification by merely simply counting the number of bright spots is difficult.

Thus, for example, Patent Document 1 describes the method of extracting the fluorescent bright spots from the fluorescent image similarly to the above method and calculating the number of particles included in each bright spot on the basis of the average luminance value per fluorescent dye accumulated particle. The method described in Patent Document 1 calculates the luminance value in each bright spot and uses the luminance value to be a mode as the average luminance value per fluorescent dye accumulated particle.

However, since the luminance value varies according to the difference of luminance per fluorescent dye accumulated particle; difference of light source intensity, microscope individual difference, difference of creation condition of fluorescent dye accumulated particles, difference of staining condition of the tissue slice to be a target, and the like, the luminance variations due to these factors need to be corrected in order to improve the accuracy of quantification. With respect to such a problem, the correction of luminance variation is performed by a method of performing sensitivity calibration of the fluorescent detector (for example, refer to Patent Document 2) and a method of performing standardization regarding the intensity of excitation light source and microscope specific factors (for example, refer to Patent Document 3).

PRIOR ART DOCUMENT

Patent Documents

Patent Document 1: International Publication No. 2012029342
Patent Document 2: Japanese Patent Application Laid Open Publication No. 2004-157018
Patent Document 3: Japanese Patent No. 5593221
Patent Document 4: International Publication No. 2016129061

DISCLOSURE OF THE INVENTION

Problems to be Solved by the Invention

The number of fluorescent dye accumulated particles adhering to the target sample varies due to the differences of the surface modification condition of the fluorescent dye accumulated particles, staining condition and activation process condition of target tissue slice and the like. The methods of Patent Documents 2 and 3 cannot cope with such variation in the adhering number.

Thus, for example, Patent Document 4 discloses the method of performing observation of culture cell for which the expression amount of protein is obvious as a standard sample, under a same condition, as the condition of target sample, and calculating the expression amount of biological substance in the standard sample from the difference in the number of fluorescent bright spots. Thus, quantitative evaluation can be performed without being influenced by the variation factors such as the staining condition.

However, in the method of Patent Document 4, since the luminance value per fluorescent dye accumulated particle is not obvious, it is difficult to calculate the expression amount of the biological substance in the standard sample due to the bright spot being not extracted or the like when the luminance of the fluorescent dye accumulated particles remarkably decreases, for example.

The present invention has been made in consideration of the above problems, and an object of the present invention is to provide a biological substance quantification method, an image processing device, a pathological diagnosis support system, and a program that enable quantitative analysis of biological substance without being influenced by the luminance variation per fluorescent dye accumulated particle or the variation in adhering number of fluorescent dye accumulated particle to the target sample.

Means for Solving the Problem

In order to achieve the above object, the biological substance quantification method described in claim 1 is a biological substance quantification method of quantifying an expression amount of a specific biological substance in a target sample that is stained by using a fluorescent dye accumulated particle bondable to the specific biological substance, the method including: an input step that is inputting a first fluorescent image obtained by image capturing of the target sample; a luminance calculation step that is extracting a bright spot portion from the first fluorescent image and calculating a first luminance value which is a luminance value of the bright spot portion; and a particle number calculation step that is calculating a number of the fluorescent dye accumulated particle included in the bright spot portion extracted from the first fluorescent image by using the first luminance value, a second luminance value and a distribution of a third luminance value, the second luminance value being a luminance value of a bright spot portion extracted from a second fluorescent image obtained by image capturing of a standard sample for which an expression amount of the specific biological substance is measured in advance, and the third luminance value being a luminance value of each bright spot portion representing light emission of the fluorescent dye accumulated particle in a third fluorescent image obtained by image capturing of a preparation on which the fluorescent dye accumulated particle is dispersed without aggregating.

The invention described in claim 2 is the biological substance quantification method according to claim 1, wherein each of the bright spot portion is a region where the fluorescent dye accumulated particle exists, the first luminance value is a first luminance integrated value that is an integrated value of the luminance value of the blight spot portion extracted from the first fluorescent image, the second luminance value is a second luminance integrated value that is an integrated value of the luminance value of the bright spot portion extracted from the second fluorescent image, and the third luminance value is a third luminance integrated value that is an integrated value of the luminance value of the bright spot portion extracted from the third fluorescent image.

The invention described in claim 3 is the biological substance quantification method according to claim 2, wherein the particle number calculation step includes: a unit luminance value calculation step that is calculating a unit luminance value per the fluorescent dye accumulated particle from the distribution of the third luminance integrated value adding up the luminance value of each of the bright spot portion representing the light emission of the fluorescent dye accumulated particle in the third fluorescent image; a tentative particle number calculation step that is calculating a tentative number of the fluorescent dye accumulated particle included in the bright spot portion extracted from the first fluorescent image by using the first luminance integrated value and the unit luminance value; and a particle number correction step that is correcting the tentative number of the fluorescent dye accumulated particle included in the bright spot portion extracted from the first fluorescent image by using the second luminance integrated value.

The invention described in claim 4 is the biological substance quantification method according to claim 2, wherein the particle number calculation step includes: a unit luminance value calculation step that is calculating a unit luminance value per the fluorescent dye accumulated particle from the distribution of the third luminance integrated value adding up the luminance value of each of the bright spot portion representing the light emission of the fluorescent dye accumulated particle in the third fluorescent image; an exposure time calculation step that is calculating an exposure time in the image capturing of each of the first fluorescent image and the second fluorescent image based on comparison between the unit luminance value and a reference luminance value per the fluorescent dye accumulated particle predicted under a predetermined condition; a tentative particle number calculation step that is calculating a tentative number of the fluorescent dye accumulated particle included in the bright spot portion extracted from the first fluorescent image by using the first luminance integrated value and the reference luminance value; and a particle number correction step that is correcting the tentative number of the fluorescent dye accumulated particle included in the bright spot portion extracted from the first fluorescent image by using the second luminance integrated value, and each of the first fluorescent image and the second fluorescent image is an image taken with the exposure time calculated by the exposure time calculation step.

The invention described in claim 5 is the biological substance quantification method according to claim 3 or 4, Wherein the particle number correction step is correcting using a particle number correction coefficient calculated from a ratio between a number of the fluorescent dye accumulated particle bonded to the bright spot portion in the second fluorescent image calculated by using the second luminance integrated value and a reference number of the fluorescent dye accumulated particle bonded to the bright spot portion predicted under a predetermined condition.

The invention described in claim 6 is the biological substance quantification method according to any one of claims 3 to 5, wherein the unit luminance value calculation step is calculating, as the unit luminance value, a third luminance integrated value which is a mode among the third luminance integrated value.

The invention described in claim 7 is the biological substance quantification method according to any one of claims 1 to 6, including a crosstalk removal step that is removing crosstalk by using a crosstalk correction coefficient calculated from a luminance ratio between a plurality of third fluorescent images each of which is the third fluorescent image, the third fluorescent images being captured with a plurality of respective filters by dispersing, without aggregating, one fluorescent dye accumulated particle which is the fluorescent dye accumulated particle, and the crosstalk being captured via a filter, among the filters, not corresponding to the one fluorescent dye accumulated particle, wherein the target sample is stained by using a plurality of types of fluorescent dye accumulated particles including the one fluorescent dye accumulated particle, the plurality of types of fluorescent dye accumulated particles having different light emission wavelengths and being capturable by using the filters corresponding to the respective light emission wavelengths.

The image processing device described in claim 8 is an image processing device that quantifies an expression amount of a specific biological substance in a target sample which is stained by using a fluorescent dye accumulated particle bondable to the specific biological substance, the device including: an input means to input a first fluorescent image obtained by image capturing of the target sample; a luminance calculation means that extracts a bright spot portion from the first fluorescent image and calculates a first luminance integrated value which is an integrated value of a luminance value of the bright spot portion; and a particle number calculation means that calculates a number of the fluorescent dye accumulated particle included in the bright spot portion extracted from the first fluorescent image by using the first luminance integrated value, a second luminance integrated value and a distribution of a third luminance integrated value, the second luminance integrated value being an integrated value of a luminance value of a bright spot portion extracted from a second fluorescent image obtained by image capturing of a standard sample for which an expression amount of the specific biological substance is measured in advance, and the third luminance integrated value adding up a luminance value of each bright spot portion representing light emission of the fluorescent dye accumulated particle in a third fluorescent image obtained by image capturing of a preparation on which the fluorescent dye accumulated particle is dispersed without aggregating.

The program described in claim 9 is a program causing a computer that quantifies an expression amount of a specific biological substance in a target sample which is stained by using a fluorescent dye accumulated particle bondable to the specific biological substance to function as: an input means to input a first fluorescent image obtained by image capturing of the target sample; a luminance calculation means that extracts a bright spot portion from the first fluorescent image and calculates a first luminance integrated value which is an integrated value of a luminance value of the bright spot portion; and a particle number calculation means that calculates a number of the fluorescent dye accumulated particle included in the bright spot portion extracted from the first fluorescent image by using the first luminance integrated value, a second luminance integrated value and a distribution of a third luminance integrated value, the second luminance integrated value being an integrated value of a luminance value of a bright spot portion extracted from a second fluorescent image obtained by image capturing of a standard sample for which an expression amount of the specific biological substance is measured in advance, and the third luminance integrated value adding up a luminance value of each bright spot portion representing light emission of the fluorescent dye accumulated particle in a third fluorescent image obtained by image capturing of a preparation on which the fluorescent dye accumulated particle is dispersed without aggregating.

The pathological diagnosis support system described in claim 10 is a pathological diagnosis support system, including: the image processing device according to claim 8; and an image acquiring device that acquires the first fluorescent image, the second fluorescent image and the third fluorescent image.

Effects of the Invention

According to the present invention, it is possible to provide a biological substance quantification method, an image processing device, a pathological diagnosis support system, and a program that enable quantitative analysis of biological substance without being influenced by the luminance variation per fluorescent dye accumulated particle or the variation in adhering number of fluorescent dye accumulated particle to the target sample.

BRIEF DESCRIPTION OF DRAWINGS

FIG. 3 is a flowchart showing an image analysis process according to a first embodiment executed by a controller in FIG. 2.

EMBODIMENTS FOR CARRYING OUT THE INVENTION

First Embodiment

A first embodiment for carrying out the present invention will now be described with reference to the attached drawings, which should not be construed to limit the present invention.

<Configuration of Pathological Diagnosis Support System 100>

Figure 1:
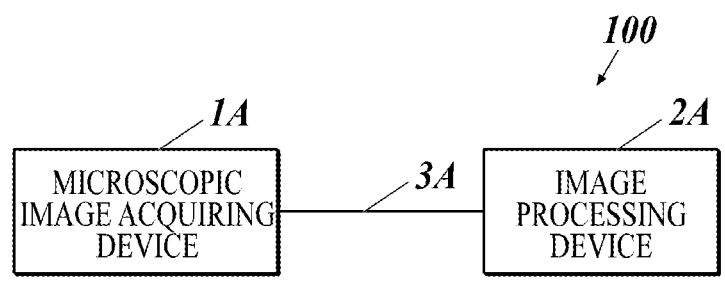
FIG. 1 is a view showing a system configuration of a pathological diagnosis support system using a biological substance quantification method of the present invention.

FIG. 1 illustrates an exemplary overall configuration of a pathological diagnosis support system 100 that employs the tissue evaluation method according to the present invention. The pathological diagnosis support system 100 acquires a microscopic image of a tissue sample stained with a predetermined staining reagent, analyzes the acquired microscopic image, and thereby outputs a feature amount which quantitatively represents expression of a specific biological substance in the tissue sample of observation target.

As illustrated in FIG. 1, in the pathological diagnosis support system 100, a microscopic image acquiring device 1A and an image processing device 2A are connected via an interface such as a cable 3A, for transmission and reception of data. The microscopic image acquiring device 1A may be connected to the image processing device 2A in any manner. For example, the microscopic image acquiring device 1A and the image processing device 2A may be connected through a local area network (LAN) or wireless communication. Furthermore, the pathological diagnosis support system 100 may be a device in which the microscopic image acquiring device 1A and the image processing device 2A are integrally formed. Images obtained by using external arbitrary devices may be input to the image processing device by using a storage such as HDD, CD and DYE).

The microscopic image acquiring device 1A is a known optical microscope provided with a camera, which acquires a microscopic image of a tissue sample on a slide placed on a slide fixation stage and functions as an image acquiring device.

The microscopic image acquiring device 1A includes au irradiation means, an imaging means, an image capturing means, and a communication interface (I/F). The irradiation means includes a light source and a filter, and emits light toward the tissue sample on the slide placed on the slide fixation stage. The imaging means includes an ocular and an objective lens. The imaging means generates an image with transmitted light, reflected light, or fluorescent light, which is emitted from the tissue sample on the slide in response to the irradiated light. The image capturing means includes a charge coupled device (CCD) sensor or the like. The image capturing means is specifically a camera disposed in a microscope to capture an image formed on an imaging surface by the imaging means, and produce the digital image data of the microscopic image. The communication interface transmits the image data of the generated microscopic image to the image processing device 2A.

The image processing device 2A analyzes the microscopic image (bright field image and fluorescent image) transmitted from the microscopic image acquiring device 1A to calculate the distribution of expression of the specific biological substance in the tissue sample of the observation target.

Figure 2:
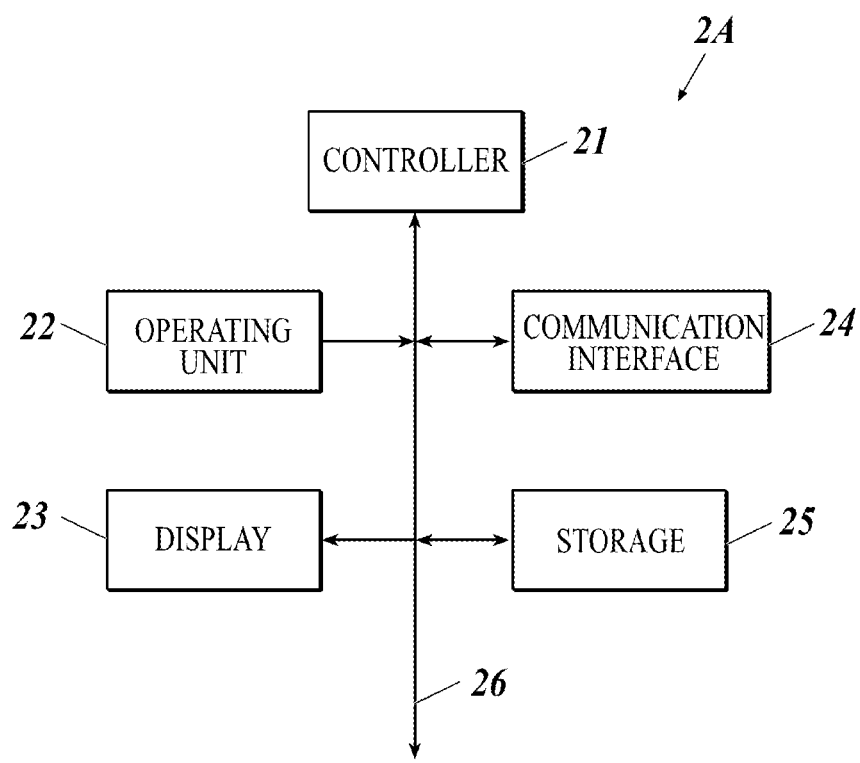
FIG. 2 is a block diagram showing the functional configuration of an image processing device in FIG. 1.

As illustrated in FIG. 2, the image processing device 2A includes a controller 21, an operating unit 22, a display 23, a communication interface 24, and a storage 25, which are connected to each other through a bus 26.

The controller 21 includes a central processing unit (CPU), a random access memory (RAM), and the like. The controller 21 executes multiple processes in cooperation with a variety of programs stored in the storage 25 to control the overall operation of the image processing device 2A. For example, the controller 21 executes an image analysis process in cooperation with a program stored in the storage 25 and functions as a means executing a luminance calculation step, a particle number calculation step, a unit luminance value calculation step, a tentative particle number calculation step, a particle number correction step, an exposure time calculation step, and a crosstalk removal step.

The operating unit 22 includes a keyboard including character input keys, numeral input keys and several functional keys, and a pointing device such as a mouse. The operating unit 22 outputs the pressing signal of the key which received the pressing operation with the keyboard and the operation signal by the mouse as input signals to the controller 21.

The display 23 includes a monitor, such as a cathode ray tube (CRT) display or a liquid crystal display (LCD). The display 23 displays a variety of windows in response to display signals input from the controller 21. The display 23 in the present embodiment functions as an output means for outputting the results of image analysis, for example.

The communication interface 24 is an interface that allows data transmission and reception With external devices such as the microscopic image acquiring device 1A. The communication interface 24 functions as a means to execute an input step.

The storage 25 includes a hard disk drive (HDD) or a nonvolatile memory composed of a semiconductor, for example. The storage 25 stores a variety of programs and data as described above.

In addition, the image processing device 2A may include a LAN adaptor and a muter to be connected to external devices through a communication network such as a LAN.

<Acquisition of Image from Tissue Sample>

Preparing of a target tissue sample (target sample) of an objective biological substance quantification according to the present invention will now be described in detail, including the staining reagent and the method of staining.

(1) Objective Biological Substance

The tissue sample according to the present invention is stained with a staining reagent including fluorescent dye accumulated particles which can stain the objective biological substance. The objective biological substance is a biological substance expressed on a tissue slice, especially protein (antigen). Typically used objective biological substances include biological substances (for example, HER2 protein) that are expressed on cell membrane of various cancer tissues and can be used as a biomarker.

(2) Fluorescent Dye Accumulated Particle

The fluorescent dye accumulated particle according to the present invention is a nano-sized particle Which emits fluorescence in response to irradiation with excitation light. The fluorescent dye accumulated particle can emit sufficiently strong fluorescence to represent each molecule of the objective biological substance as a bright spot.

The fluorescent dye accumulated particle may have an arbitrary emission wavelength within the sensitivity range of the image capturing element of the fluorescence microscope. Specifically, an emission wavelength of 400 to 700 nm is preferable.

The fluorescent dye accumulated particle may have any average particle size. When the particle size is large, it is not easy to access the antigen. When the particle size is small and the luminance value is low, the emitted fluorescence may be buried in background noise (e.g. noise of a camera and autofluorescence of cells). Accordingly, the fluorescent dye accumulated particle may preferably have an average particle size in around the range of 20 to 200 nm.

The coefficient of variation of the particle size is preferably 15% or less. Since the variation in particle size of fluorescent dye accumulated particle is small, the luminance value of fluorescence per particle is nearly constant, which improves the accuracy of quantification.

As for the average particle size, the cross-sectional area is measured for a sufficient number of particles in an electron microscopic photograph taken with a scanning electron microscope (SEM). The each measured value is regarded as the area of a circle, and the diameter of the circle is determined as the particle size. In the present application, the particle sizes of 1000 particles are measured, and the arithmetic average is determined as the average particle size. The variation coefficient is also calculated based on the particle size distribution of 1000 particles.

The fluorescent dye accumulated particle is a nano-sized particle containing an organic or inorganic particle as a base material and further having a plurality of fluorescent dyes contained in the particle and/or adsorbed on the surface of the particle.

A preferable fluorescent dye accumulated particle includes the base material and the fluorescent dye having a substituent group or a site having opposite electric charge from each other, to cause an electrostatic interaction.

(2.1) Base Material

Examples of an organic base material include resins generally classified into thermosetting resins, such as melamine resins, urea resins, aniline resins, guanamine resins, phenol resins, xylene resins, and furan resins; resins generally classified into thermoplastic resins, such as styrene resins, acrylic resins, acrylonitrile resins, AS resins (acrylonitrile-styrene copolymer resin), and ASA resins (acrylonitrile-styrene-methyl acrylate copolymer resin); other resins such as polylactic acid; and polysaccharides.

Examples of an inorganic base material include silica, glass, and the like.

Particularly, using a melamine resin as the base material is preferable since it is possible to suppress the variation in particle size compared to using silica and the like.

(2.2) Fluorescent Dye Accumulated Particle

The fluorescent dye accumulated particle has fluorescent dye contained in the base material and/or adsorbed on the surface of the base material.

Examples of the fluorescent dye include rhodamine-based dye molecules, squarylium-based dye molecules, cyanine-based dye molecules, aromatic ring-based dye molecules, oxazine-based dye molecules, carbopyronine-based dye molecules, and pyrromethene-based dye molecules.

Examples of the fluorescent dye include Alexa Fluor (registered trademark, made by Invitrogen Corporation) dye molecules, BODIPY (registered trademark, made by Invitrogen Corporation) dye molecules, Cy (registered trademark, made by GE Healthcare) dye molecules, HiLyte (registered trademark, made by AnaSpec Inc.) dye molecules, DyLight (registered trademark, made by Thermo Scientific Inc.) dye molecules, ATTO (registered trademark, made by ATTO-TEC GmbH.) dye molecules, MFP (registered trademark, made by Mobitec Inc.) dye molecules, CF (registered trademark, made by Biotium Inc.) dye molecules, DY (registered trademark, made by Dyomics GmbH) dye molecules. CAL (registered trademark, made by Bio-Search Technologies Inc.) dye molecules, and the like.

When the fluorescent dye is contained in the base material, the fluorescent dye may be dispersed within the base material in any form. The fluorescent dye and the base material may or may not be chemically bonded with each other.

(2.3) Quantum Dot Accumulated Particle

In the present invention, the quantum dot accumulated particle may be used as the fluorescent dye accumulated particle.

The quantum dot accumulated particle has the quantum dot contained in the base material and/or adsorbed on the surface of the base material.

The quantum dot may be a semiconductor nanoparticle containing Group II-VI compounds, Group III-V compounds, or Group IV elements. Specific examples thereof include CdSe, CdS, CdTe, ZnSe, ZnS, ZnTe, InP, InN, InAs, InGaP, GaP, GaAs, Si, and Ge.

If the quantum dots are contained in the base material, the quantum dots may be dispersed within the base material in any form. The quantum dots and the base material may or may not be chemically bonded with each other.

(3) Staining Reagent (Antigen-Fluorescent Dye Accumulated Particle Conjugate)

The staining reagent is designed such that a single fluorescent dye accumulated particle is bonded to a single objective biological substance.

As for the staining reagent (immunostaining reagent) used for immunostaining, for improving the efficiency of fluorescence labelling and reducing the time which results in deterioration of fluorescence, the immunostaining reagent is preferably a complex in which a primary antibody is connected to a fluorescent dye accumulated particle indirectly, that is, not by a covalent bond but by a bond using antigen-antibody reaction and the like. In order to make the staining operation easier, the immunostaining reagent may be a complex in which a primary antibody or a secondary antibody is connected to a fluorescent dye accumulated particle directly.

An exemplary immunostaining reagent may be described as follows: [a primary antibody against the Objective biological substance] . . . [an antibody (secondary antibody) against the primary antibody]~[a fluorescent dye accumulated particle]

The description " . . . " represents a bond by an antibody-antigen interaction. The description "~" represents a non-limited bond, for example, a covalent bond, an ionic bond, a hydrogen bond, a coordination bond, an antibody-antigen interaction, a biotin-avidin interaction, physical adsorption, chemical adsorption, and the like. If necessary, a bond via a linker molecule may be used.

A primary antibody to be used includes an antibody which specifically recognizes and bonds to the objective biological substance as an antigen. For example, anti-HER2 antibody can be used when HER2 is the objective biological substance, and anti-HER3 antibody can be used when HER3 is the objective biological substance.

A secondary antibody to be used includes an antibody which specifically recognizes and bonds to the primary antibody.

Animals (immunized animals) for producing antibodies are not particularly limited, and can be selected from any conventionally used animals, such as mouse, rat, guinea pig, rabbit, coat, and sheep.

(4) Staining Method of Tissue Sample

An exemplary staining method of tissue sample will be explained by taking, as an example, staining of a paraffin-embedded tissue slice (hereinafter may be simply referred to as a "slice"). However, as the tissue sample according to the present invention, an arbitrary sample such as a sample obtained by needle biopsy may be used.

(4.1) Production Step of Sample (4.1.1) Deparaffinization Process

A slice is immersed in a container containing xylene so that paraffin is removed. The temperature is not particularly limited, and the process can be performed at room temperature. Preferably, the immersing time is 3 minutes or more and 30 minutes or less. The xylene may be changed during the immersion as needed.

Next, the slice is immersed in a container containing ethanol so that the xylene is removed. The temperature is not particularly limited, and the process can be performed at room temperature. Preferably, the immersing time is 3 minutes or more and 30 minutes or less. The ethanol may be changed during the immersion as needed.

The slice is immersed in a container containing water so that the ethanol is removed. The temperature is not particularly limited, and the process can be performed at room temperature. Preferably, the immersing time is 3 minutes or more and 30 minutes or less. The water may be changed during the immersion as needed.

(4.1.2) Activation Process

In accordance with a publically-known method, the objective biological substance is subjected to an activation process. The activation process can be performed under any condition. As for an activating solution, a 0.01 M citrate buffer solution (pH 6.0), a 1 mM EDTA solution (pH 8.0), 5% urea, a 0.1 M Tris-hydrochloride buffer solution, and the like can be used.

The activation process is performed under a condition of pH 2.0 to 13.0 depending on the kind of the tissue slice, such that a signal is emitted and the damage of the tissue is in a degree allowing evaluation of the signal. The activation process is usually performed at pH 6.0 to 8.0, but is performed at pH 3.0, for example, in the case of a special tissue slice.

As for a heater, an autoclave, a microwave heater, a pressure cooker, a water bath, or the like can be used. The temperature is not particularly limited. The temperature may range from 50 to 130° C., and the tithe may range from 5 to 30 minutes. The process can be performed at room temperature.

Subsequently, the slice after the activation process is immersed in a container including PBS and washed. The temperature is not particularly limited, and the process can be performed at room temperature. Each immersion time is preferably 3 minutes or more and 30 minutes or less. The PBS may be changed during the immersion as needed.

(4.2) Immunostaining Step

In the immunostaining step for staining the objective biological substance, a solution of immunostaining reagent including a fluorescent dye accumulated particle having a site which can directly or indirectly bond to the objective biological substance is put on the slice, to cause reaction with the objective biological substance. The solution of the immunostaining reagent used in the immunostaining step may be prepared in advance before the immunostaining step.

The conditions for the immunostaining step, i.e. the temperature and time of immersing the tissue sample in the solution of the immunostaining reagent, can be suitably adjusted according to the conventional immunostaining method, so that appropriate signals can be obtained.

The temperature is not particularly limited, and the process can be performed at room temperature. Preferably, the reaction time is 30 minutes or more and 24 hours or less.

Before performing the above-described process, it is preferable to add a known blocking reagent such as PBS including BSA and a surfactant such as Tween 20.

(4.3) Post-Processing Step of Sample

After the immunostaining step, the tissue sample is preferably subjected to processes such as fixation-dehydration, permeation, and encapsulation so that the tissue sample becomes suitable for the observation.

The fixation-dehydration process is performed by immersing the tissue sample in a solution for fixation process (crosslinking reagent such as formalin, paraformaldehyde, glutaraldehyde, acetone, ethanol, and methanol). The permeation process is performed by immersing the tissue sample after the fixation-dehydration process in a solution for permeation (such as xylene). The encapsulation process is performed by immersing the tissue sample after the permeation process in a solution for encapsulation.

The conditions for these processes, for example, the temperature and tune of immersing the tissue sample in the prescribed solution, can be suitably adjusted so that appropriate signals can be obtained, according to the conventional immunostaining method.

(4.4) Staining Step for Morphological Observation

Apart from the immunostaining step, staining for morphological observation is performed for easily observing morphology of a cell, tissue, and organ in a bright field. The staining step for morphological observation can be performed according to a known arbitrary method, before or after the immunostaining step.

For morphological observation of the tissue sample, staining by eosin is generally performed for staining cytoplasm, stroma, various fibers, red blood cell, and keratinocyte in red to dark red. Staining by hematoxylin is also generally performed for staining a cell nucleus, calcification portion, cartilage, bacteria, and mucus in livid to light blue. (The method to perform these two staining simultaneously is known as hematoxylin-eosin staining (HE staining))

<Acquisition of Image from Standard Sample>

Next, preparing of a standard sample will be described, the standard sample being used in correction of the number of fluorescent dye accumulated particles adhering to the cell.

Hereinafter, the description is made by taking; as an example; a case where a standard sample is a cell cultured on a substrate such as a commercially available microscopic slide and expresses the objective biological substance.

(1) Quantification of Objective Biological Substance

First, an operator quantifies the concentration of the objective biological substance in the cultured cell, which is the standard sample of the present embodiment. The concentration of the objective biological substance can be quantified by any known method, for example, ELISA, flow cytometry. Western blotting, and the like. The concentration of the objective biological substance per cell can be thereby calculated. According to ELISA and Western blotting, the objective biological substance can be quantified from cells dissolved in a predetermined solution. According to flow cytometry, biological molecules per cell can be detected and quantified from cells scattered in a predetermined solution by light scattering or fluorescence quantification with laser beam.

(2) Staining of Standard Sample

As a standard sample, the operator selects cultured cells in the same lot and having the same quality as the cultured cells in which concentration of the objective biological substance is quantified. Any number of kinds of standard samples may be selected. In order to obtain a highly accurate quantification result by making calibration curves based on the quantification result from the standard samples, a plurality of kinds of standard samples are preferably used, the plurality of kinds of standard samples preferably having widely different concentration of objective biological substance quantified in advance.

The standard sample is obtained by performing immunostaining and morphological observation staining to the cultured cell under the same condition as the condition of the staining of tissue slice. Since these staining methods are similar to the staining methods of tissue slice ((4.2) Immunostaining Step, and (4.4) Staining Step for Morphological Observation), the detailed explanation is omitted. Staining under the same condition means that, for example, one operator performs staining process using staining reagents in the same lot, and that the time, temperature, and humidity in each staining are substantially constant. It is preferred that one operator performs staining of the standard sample and the tissue sample sequentially and in parallel using the staining reagents in the same lot, so that the staining conditions can be easily same.

<Production of Fluorescent Dye Accumulated Particle-Dispersed Preparation>

Next, a fluorescent dye accumulated particle-dispersed preparation, which is used for calculating an average luminance value per fluorescent dye accumulated particle, will be described.

Hereinafter, a production step for the fluorescent dye accumulated particle-dispersed preparation will be specifically described, but any fluorescent dye accumulated particle-dispersed preparation may be used as the fluorescent dye accumulated particle-dispersed preparation of the present invention, as long as the fluorescent dye accumulated particles are dispersed while avoiding aggregation.

[Production Method]

(1) Fluorescent dye accumulated particles with a given average particle size (for example, 150 nm) are provided.

(2) The fluorescent dye accumulated particles are diluted with PBS to produce a solution of the fluorescent dye accumulated particles with a concentration of 0.005 nM.

(3) A slide glass is provided.

(4) Onto the slide glass, 7.5 uL of the solution of the fluorescent dye accumulated particles is dripped such that the dripping area is substantially equivalent to the area of a circle with the diameter of 5.0 mm.

(5) The slide glass is allowed to stand still for 10 minutes.

(6) The slide glass is immersed in a 300 mL beaker containing pure water and washed.

(7) The slide glass is fitted to a staining basket and washed with running water for 10 minutes.

(8) The staining basket is taken out from water and is passed through three ethanol phases for dehydration and three xylene phases for xylene replacement.

(9) The slide glass is mounted with a xylene mounting agent (marinol).

In the production method, it is possible to control the density of the fluorescent dye accumulated particles by changing, for example, the concentration of the solution of the fluorescent dye accumulated particles. A particle density in the fluorescent dye accumulated particle-dispersed preparation is preferably $10^6$ counts/mm$^2$ or less.

The standard sample and the dispersed fluorescent accumulated particles may be prepared on a same slide as a control slide. This case is efficient since the work of changing slide can be omitted. In the present embodiment, a control slide preparing both of the standard sample and the dispersed fluorescent dye accumulated particles is used for analysis.

<Operation of Pathological Diagnosis Support System 100 (Including Image Processing Method)>

Hereinafter, analytical operation in the pathological diagnosis support system 100, based on the fluorescent images and the bright field images photographing the above mentioned tissue sample, standard sample, and control slide onto which the fluorescent dye accumulated particles are dispersed, will be described, but the image processing of the present invention is not limited to this.

At first, an operator stains the standard sample and the tissue sample with a hematoxylin staining reagent and a staining reagent using fluorescent dye accumulated particles that bind to the objective biological material. Furthermore, a control slide is provided, the control slide being obtained by dispersing, on the same slide glass as the slide glass of the standard sample, fluorescent dye accumulated particles that have been produced in the same manner as the fluorescent dye accumulated particles used for staining the tissue sample and the standard sample.

Then, by using the microscopic image acquiring device 1A, a bright field image (first bright field image) and a fluorescent image (first fluorescent image) of the tissue sample, a bright field image (second bright field image) and a fluorescent image (second fluorescent image) of the standard sample, and a fluorescent image (third fluorescent image) of the fluorescent dye accumulated particles which are dispersed (hereinafter, referred to as dispersed particles) are acquired, and data for the respective images are transmitted to the image processing device 2A.

FIG. 3 shows a flowchart of an image analysis process in the image processing device 2A. The image analysis process shown in FIG. 3 is executed by cooperation of the controller 21 and a program stored in the storage 25.

When a first bright field image is inputted from the microscopic image acquiring device 1A by the communication interface 24 (Step S301), a first cell nucleus image in which a region of the cell nucleus is extracted from the first bright field image is created (Step S302). In Step S302, the extraction may be performed by using any known methods, and any region, without being limited to the cell nucleus, may be extracted as a region of interest (ROI).

When a first fluorescent image is inputted from the microscopic image acquiring device 1A by the communication interface 24 (Step S303: input step), a first bright spot region image in which a bright spot region (bright spot portion) representing light emission of the fluorescent dye accumulated particles is extracted from the first fluorescent image is created by the controller 21 (Step S304). Next, a first luminance integrated value for each bright spot region in the first bright spot region image is calculated by the controller 21 (Step S305: luminance calculation step).

In the processes of Steps S304 to S305, measurement can be performed by using any known methods, such as an open analytical software, ImageJ, and an automatic measuring software for all bright spots manufactured by G-Angstrom Co., Ltd., G-Count.

When a second bright field image is inputted from the microscopic image acquiring device 1A by the communication interface 24 (Step S306), a second cell nucleus image in which a region of the cell nucleus is extracted from the second bright field image is created by the controller 21 (Step S307).

When a second fluorescent image is inputted from the microscopic image acquiring device 1A by the communication interface 24 (Step S308), a second bright spot region image in which a bright spot region (bright spot portion) representing light emission of the fluorescent dye accumulated particle is extracted from the second fluorescent image is created by the controller 21 (Step S309). Next, a second luminance integrated value for each bright spot region in the second bright spot region image is calculated by the controller 21.

Figure 4A:
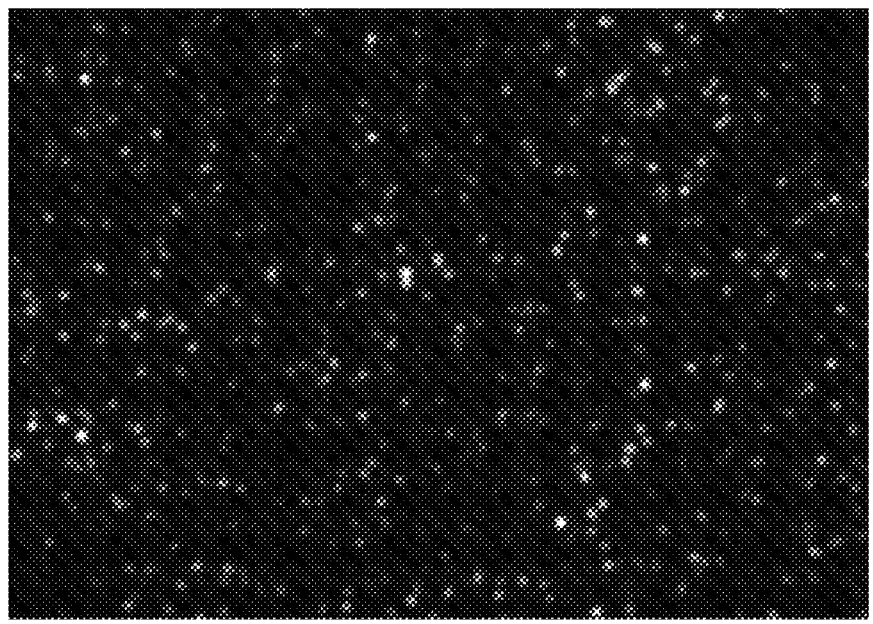
FIG. 4A is a view showing an example of a third fluorescent image.
Figure 4B:
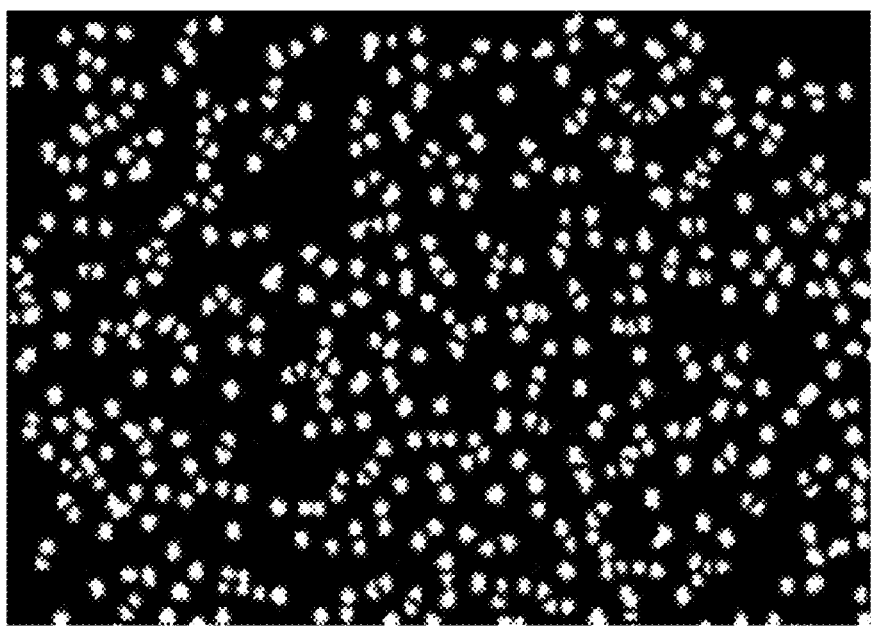
FIG. 4B is a view showing an example of a third bright spot region image.

When a third fluorescent image (FIG. 4A) is inputted from the microscopic image acquiring device 1A by the communication interface 24 (Step S311), a third bright spot region image (FIG. 4B) in which bright spot regions (bright spot portions) representing light emission of the fluorescent dye accumulated particles are extracted from the third fluorescent image is created by the controller 21 (Step S312). A third luminance integrated value for each bright spot region is calculated (Step S313).

Specifically, when the third bright spot region image is generated (FIG. 4B), there is created a luminance distribution numerically expressing the luminance values at X-coordinate positions and Y-coordinate positions for each bright spot region. The third luminance integrated value in the bright spot region is obtained by multiplying these values.

Figure 5:
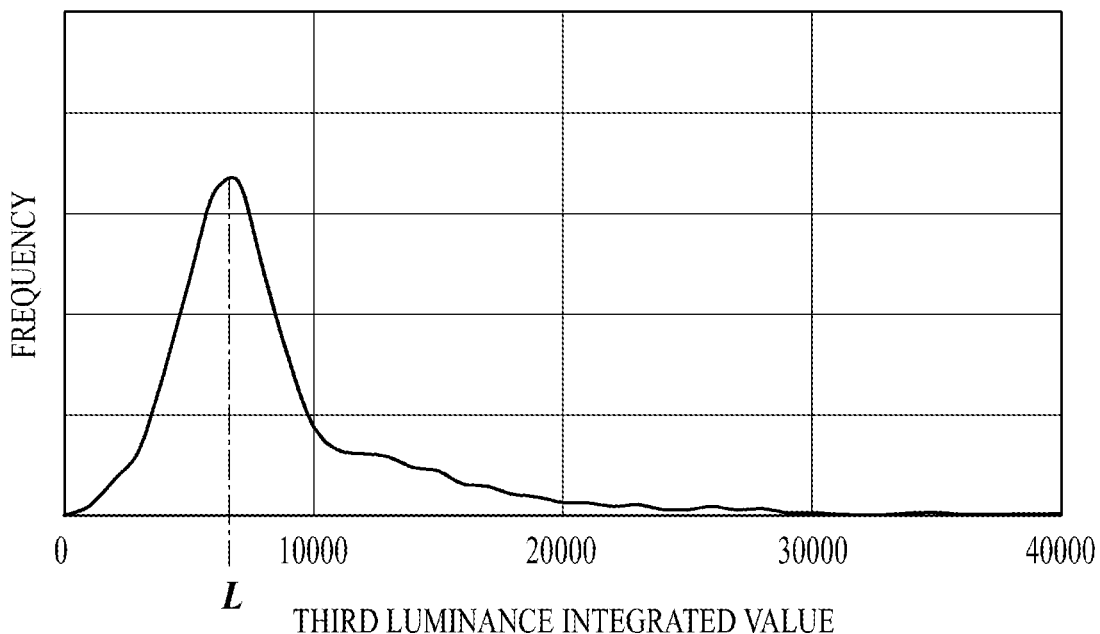
FIG. 5 is an example of a luminance distribution curve.

Based on the distribution of the third luminance integrated values, an average luminance value per fluorescent dye accumulated particle is calculated by the controller 21 (Step S314: unit luminance value calculation step). In particular, as shown in FIG. 5, the luminance distribution curve is created with the third luminance integrated value of the bright spot region in the third bright spot region image as a horizontal axis, and the frequency of the luminance integrated value as a vertical axis. Based on this luminance distribution curve, for example, a third luminance integrated value to be the mode (a luminance integrated value L at the peak of the luminance distribution curve) is calculated as the average luminance value. Instead of the luminance distribution curve, a histogram indicating the frequency of the third luminance integrated value may be created.

From a viewpoint of enhancing the accuracy of the calculated average luminance value, it is preferable that the third luminance integrated values be calculated from 10000 or more bright spot regions in Step S314 (unit luminance value calculation step) and that the average luminance value be calculated based on their distribution.

In addition, for the calculation of the mode, it is preferable that fitting or interpolation be performed to the distribution of the third luminance integrated values and that a luminance integrated value at the peak of the fitting curve or the interpolation curve is used as the average luminance value. The distribution of the third luminance integrated values of the present invention can be suitably fitted to, for example, a Gaussian curve, a quadratic curve, a Poisson distribution, a binomial distribution or the like.

After the processes of steps S305 and S314 are finished, the controller 21 calculates the number of the fluorescent dye accumulated particles included in each bright spot region of the first bright spot region image from the average luminance value per fluorescent dye accumulated particle and the first luminance integrated value in each bright spot region of the first bright spot region image (step S315). In particular, for example, the value obtained by dividing the first luminance integrated value in each bright spot region by the average luminance value is the number of fluorescent dye accumulated particles in each bright spot region. By the process of step S315, the number of fluorescent dye accumulated particles is obtained, the number of fluorescent dye accumulated particles being calculated after correction of the variation in luminance per fluorescent dye accumulated particle.

After the processes of steps S302 and S315 are finished, an addition process of the first cell nucleus image and the first bright spot region image is performed by the controller 21 (step S316), and the number of fluorescent dye accumulated particles per cell nucleus is calculated (step S317: tentative particle number calculation step).

After the processes of steps S310 and S314 are finished, the number of fluorescent dye accumulated particles included in each bright spot region of the second bright spot region image is calculated from the average luminance value per fluorescent dye accumulated particle an the second luminance integrated value of each bright spot region of the second bright spot region image by the controller 21 (step S318).

After the processes of steps S307 and S318 are finished, an addition process of the second cell nucleus image and the second region image is performed by the controller 21 (step S319), and the number of fluorescent dye accumulated particles per cell nucleus is calculated (step S320).

The particle number correction coefficient (correction coefficient) is then calculated from the ratio between the reference number of fluorescent dye accumulated particles and the number of fluorescent dye accumulated particles per cell nucleus in the standard sample obtained in step S320 by the controller 21 (step S321). The reference number of fluorescent dye accumulated particles is the number of fluorescent dye accumulated particles bonded per cell nucleus, which is predicted under the experimental condition in the present embodiment. That is, since the number of the fluorescent due accumulated particles adhering to the objective biological substance varies depending on various conditions of the experiment site, more accurate value can be obtained by calculating the correction coefficient for correcting the number of adhering fluorescent dye accumulated particles by using the number of particles in the standard sample and thereby correcting the number of florescent dye accumulated particles in the tissue sample. The particle number correction coefficient can be represented by a linear function.

After the processes of steps S317 and S321 are finished, the number of fluorescent dye accumulated particles per cell nucleus calculated in step S317 is corrected by using the particle number correction coefficient calculated in step S321 by the controller 21 (step S322: particle number correction step). In particular, the value obtained by substituting the number of fluorescent dye accumulated particles per cell nucleus for the particle number correction coefficient is the number of fluorescent dye accumulated parties. By the process of step S322, the number of fluorescent dye accumulated particles per cell nucleus is calculated, the number of fluorescent dye accumulated particles per cell nucleus being obtained by correcting the variation in the number of adhering to cell.

According to the first embodiment of the present invention which has been described above, the average luminance value as the unit luminance value is calculated from the distribution of the third luminance integrated values in the third fluorescent image, the number of fluorescent dye accumulated particles per cell nucleus is calculated by using the first luminance integrated value and the average luminance value, and this calculated value is corrected by using the second luminance integrated value. Accordingly, it is possible to accurately perform quantitative analysis of the expression amount of the objective biological substance without being influenced by the variation in luminance per fluorescent dye accumulated particle or the variation in the adhering number of the fluorescent dye accumulated particles to the target sample.

Second Embodiment

A second embodiment for carrying out the present invention will now be described with reference to the attached drawings, which should not be construed to limit the present invention.

In the first embodiment, the number of fluorescent dye accumulated particles in each of the bright spot regions of the first fluorescent image and the second fluorescent image is corrected by the average luminance value per fluorescent dye accumulated particle in the third fluorescent image. However, in the present embodiment, the exposure time in acquiring the first fluorescent image and the second fluorescent image is corrected on the basis of the average luminance value per fluorescent dye accumulated particle, and thereby in the subsequent observation, the analysis can be performed while maintaining all the luminance values constant.

Since <Configuration of Pathological diagnosis Support System 100>, <Acquisition of Image from Tissue Sample>, <Acquisition of Image from Standard Sample> and <Production of Fluorescent Dye Accumulated Particle-dispersed Preparation> are similar to those of the first embodiment, the detailed description thereof is omitted.

<Operation of Pathological Diagnosis Support System 100 (Including Image Processing Method)>

Hereinafter, analytical operation in the pathological diagnosis support system 100 based on the fluorescent images and the bright field images photographing the above mentioned tissue sample, the standard sample, and the dispersed particles will be described, but the image process of the present invention is not limited to this.

Figure 6:
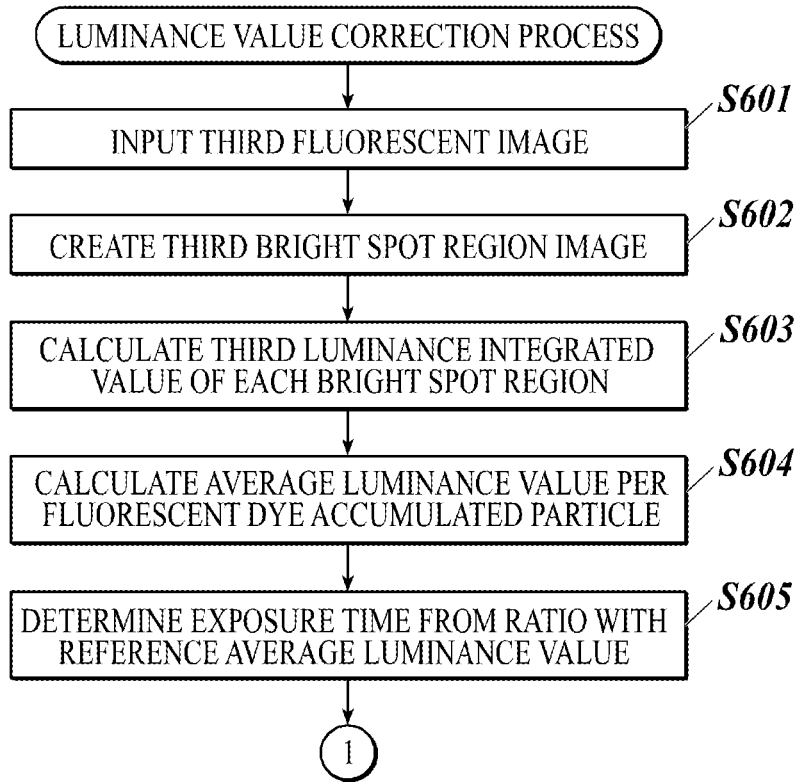
FIG. 6 is a flowchart showing a luminance value correction process according to a second embodiment executed by the controller in FIG. 2.
Figure 7:
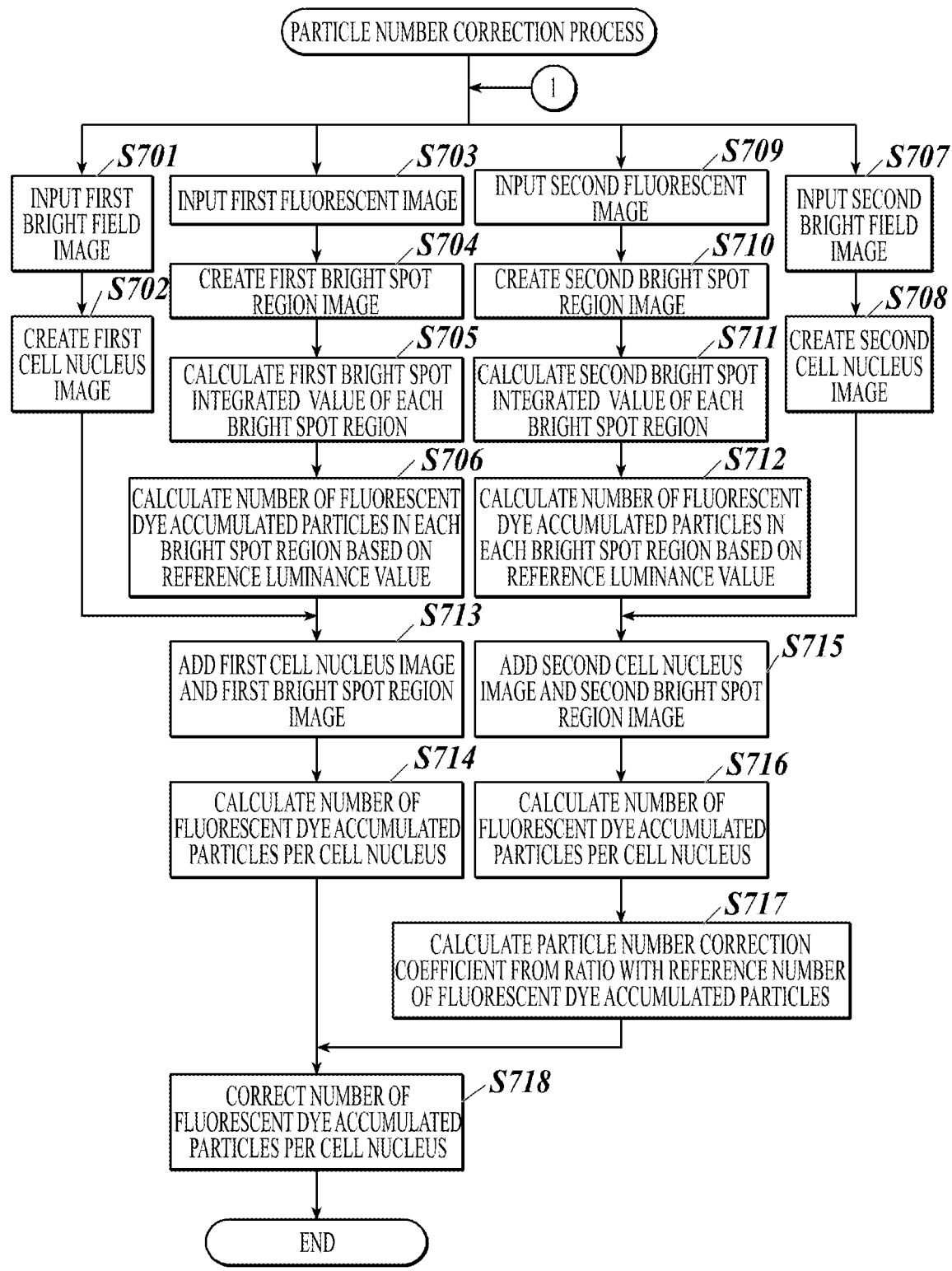
FIG. 7 is a flowchart showing a particle number correction process according to the second embodiment executed by the controller in FIG. 2.

Each of FIGS. 6 and 7 shows a flowchart of an image analysis process in the image processing device 2A. The image analysis process shown in each of FIGS. 6 and 7 is executed by cooperation of the controller 21 and a program stored in the storage 25. FIG. 6 shows the flowchart related to luminance value correction process and FIG. 7 shows a flowchart related to particle number correction process.

The image analysis process according to the second embodiment includes the luminance value correction process and the particle number correction process. The luminance value correction process shown in FIG. 6 is a process for determining the exposure time in image capturing of the first fluorescent image and the second fluorescent image using the microscopic image acquiring device 1A. The particle number correction process shown in FIG. 7 is a process of calculating and correcting the number of fluorescent dye accumulated particles per cell nucleus in the tissue sample by calculating the particle number correction coefficient using the standard sample, similarly to the first embodiment.

When the third fluorescent image is inputted from the microscopic image acquiring device 1A by the communication interface 24 (Step S601), a third bright spot region image in which a bright spot region representing light emission of the fluorescent dye accumulated particle is extracted from the third fluorescent image is created by the controller 21 (Step S602), and a third luminance integrated value for each bright spot region is calculated (Step S603). Next, based on the distribution of the second luminance integrated values, an average luminance value per fluorescent dye accumulated particle is calculated by the controller 21 (Step S604: unit luminance value calculation step).

The exposure time in image capturing of the first fluorescent image and the second fluorescent image is then determined from the ratio between the reference luminance value and the average luminance value calculated in step S604 by the controller 21 (step S605: exposure time calculation step). The reference luminance value is the luminance value per fluorescent dye accumulated particle, which is predicted under a predetermined image capturing condition including the exposure time. Since the luminance of the fluorescent dye accumulated particle is variable according to the exposure time, by correcting the exposure time, it is possible to align the average luminance value per fluorescent dye accumulated particle of the first fluorescent image and the second fluorescent image with the reference luminance value.

In particular, for example, the exposure time in image capturing of the first fluorescent image and the second fluorescent image can be calculated by calculating the ratio of reference luminance value to the average luminance value of the third fluorescent image and adding this to the exposure time under image capturing condition of the third fluorescent image.

FIG. 7 shows a flowchart of particle number correction process in the image processing device 2A. The particle number correction process shown in FIG. 7 is executed by cooperation of the controller 21 and a program stored in the storage 25.

When the first bright field image is inputted from the microscopic image acquiring device 1A by the communication interface 24 (Step S701), a first cell nucleus image in which a region of the cell nucleus is extracted from the first bright field image is created (Step S702).

When the first fluorescent image is inputted from the microscopic image acquiring device 1A by the communication interface 24 (Step S703: input step), a first bright spot region image in which a bright spot region representing light emission of the fluorescent dye accumulated particle is extracted from the first fluorescent image is created by the controller 21 (Step S704). Next, a first luminance integrated value for each bright spot region in the first bright spot region image is calculated by the controller 21 (Step S705: luminance calculation step).

After the process of step S705 is finished, the controller 21 calculates the number of the fluorescent dye accumulated particles included in each bright spot region of the first bright spot region image from the reference luminance value per fluorescent dye accumulated particle and the first luminance integrated value in each bright spot region of the first bright spot region image (step S706). In particular, for example, the value obtained by dividing the first luminance integrated value in each bright spot region by the reference luminance value is the number of fluorescent dye accumulated particles in each bright spot region.

When the second bright field image is inputted from the microscopic image acquiring device 1A by the communication interface 24 (Step S707), a second cell nucleus image in which a region of the cell nucleus is extracted from the second bright field image is created by the controller 21 (Step S708).

When the second fluorescent image is inputted from the microscopic image acquiring device 1A by the communication interface 24 (Step S709), a second bright spot region image in which a bright spot region representing light emission of the fluorescent dye accumulated particle is extracted from the second fluorescent image is created by the controller 21 (Step S710). Next, a second luminance integrated value for each bright spot region in the second bright spot region image is calculated by the controller 21 (Step S711).

After the process of step S711 is finished, the number of fluorescent dye accumulated particles included in each bright spot region of the second bright spot region image is calculated from the reference luminance value per fluorescent dye accumulated particle and the second luminance integrated value of each bright spot region of the second bright spot region image by the controller 21 (step S712).

Since the processes of Steps S713 to S714 and Steps S715 to S717 are respectively similar to the processes of Steps S316 to S317 and Steps S319 to S321 in FIG. 3, the detailed description is omitted.

The second embodiment of the present invention which has been described above includes an exposure time calculation step of calculating the exposure time in image capturing of the first fluorescent image and the second fluorescent image based on comparison of the average luminance value with the reference luminance value per fluorescent dye accumulated particle which is predicted under a predetermined condition. Accordingly, after the correction of exposure time, image capturing of the tissue sample and the standard sample is performed in a state in which the luminance value is always constant, and thus, it is not necessary to correct the luminance value for each image capturing, which is efficient.

Third Embodiment

A third embodiment for carrying out the present invention will now be described with reference to the attached drawings, which should not be construed to limit the present invention.

In the first and second embodiments, the tissue sample and the standard sample are stained by using a single fluorescent dye accumulated particle with respect to one objective biological substance. However, in the third embodiment, two or more types of the fluorescent dye accumulated particles having light emission wavelengths different from each other are used with respect to a plurality of objective biological substances to perform staining of each of the objective biological substances.

Since <Configuration of Pathological diagnosis Support System 100>, <Acquisition of Image from Tissue Sample>, <Acquisition of Image from Standard Sample> and <Production of Fluorescent Dye Accumulated Particle-dispersed Preparation> are similar to those of the first embodiment, the detailed description thereof is omitted.

<Operation of Pathological Diagnosis Support System 100 (Including Image Processing Method)>

Hereinafter, analytical operation in the pathological diagnosis support system 100 based on the fluorescent images and the bright field images photographing the above mentioned tissue sample, the standard sample, and the dispersed particles will be described, but the image process of the present invention is not limited to this.

Figure 8:
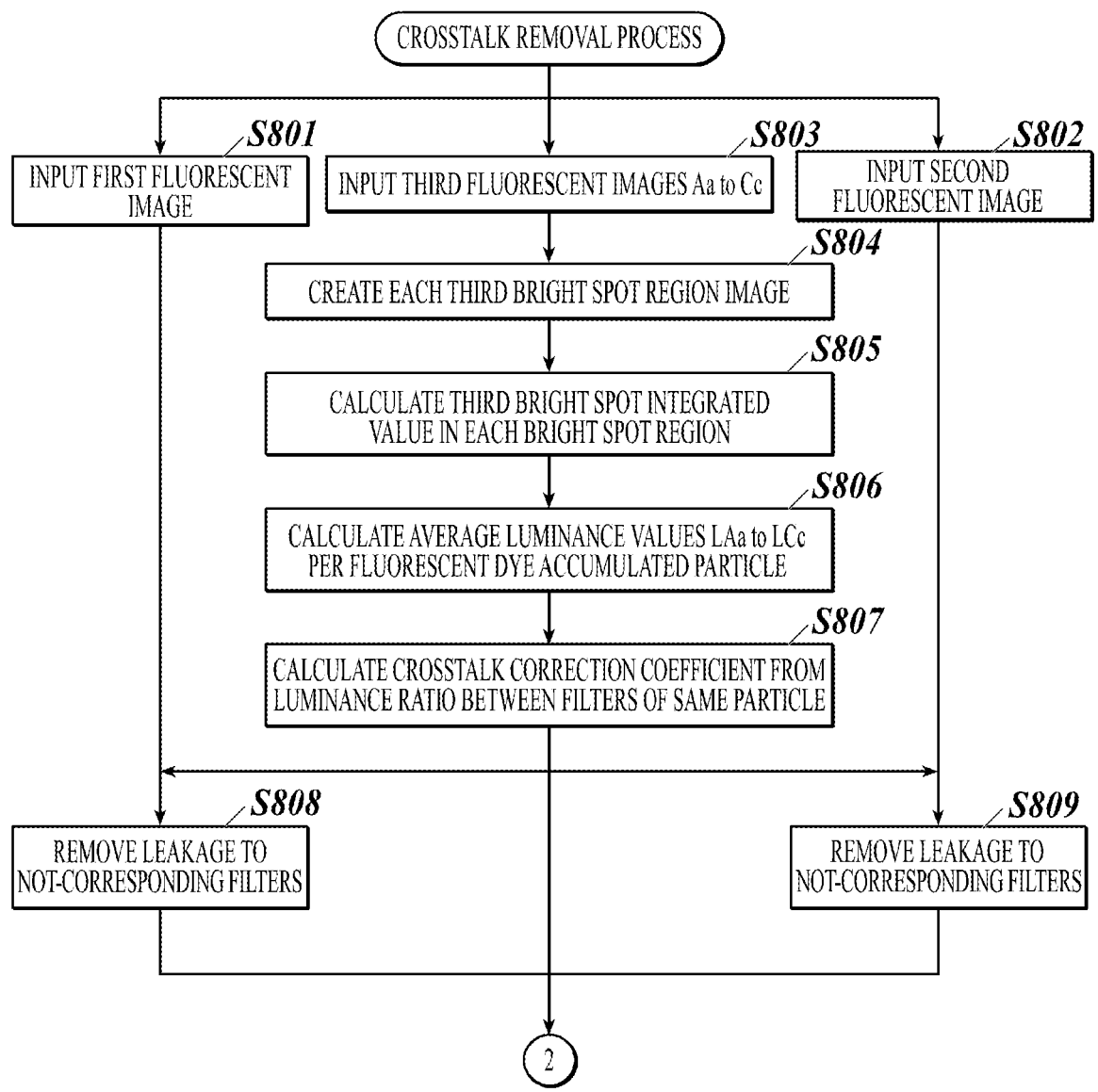
FIG. 8 is a flowchart showing a crosstalk removal process according to a third embodiment executed by the controller in FIG. 2.
Figure 9:
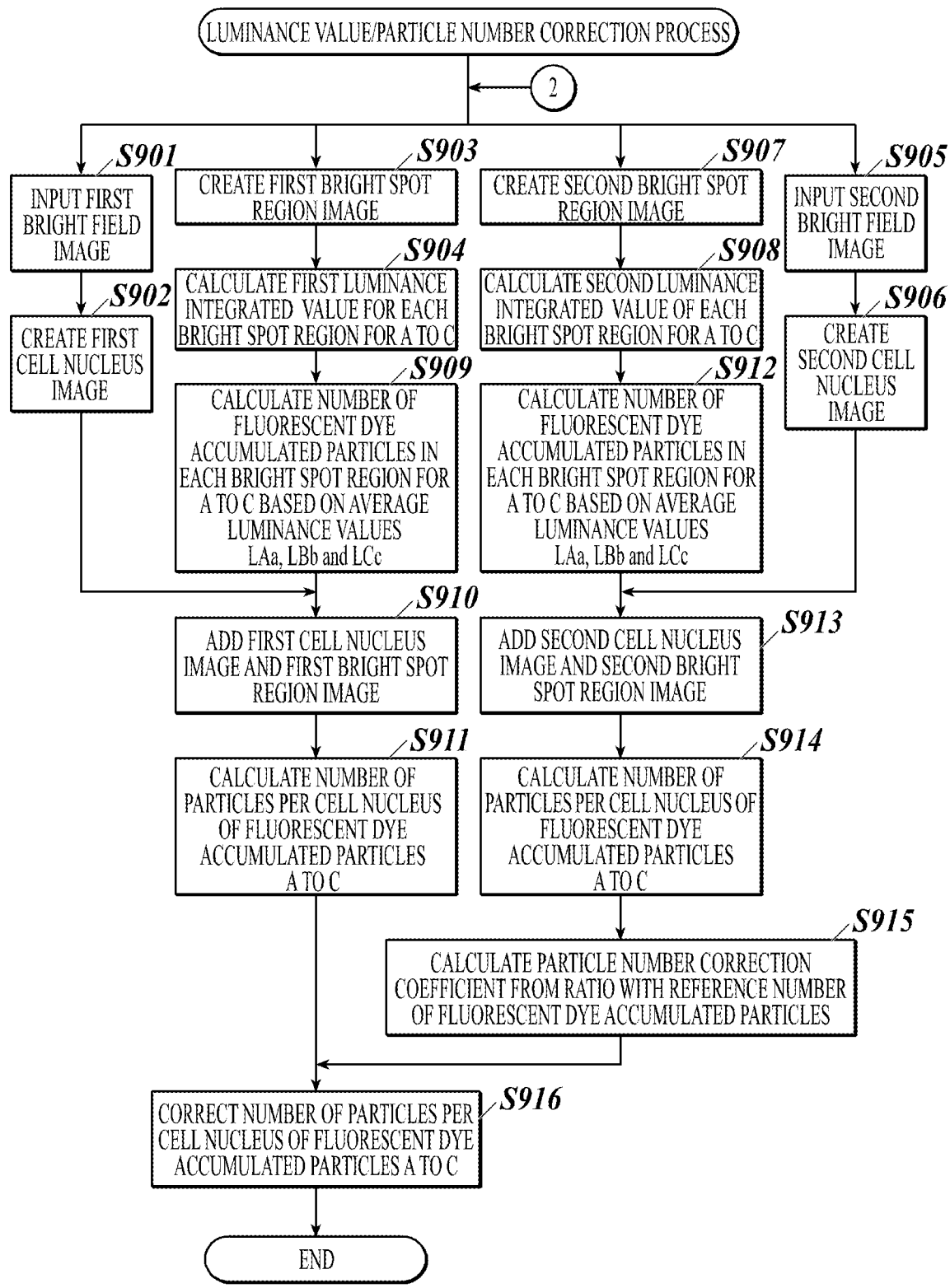
FIG. 9 is a flowchart showing a luminance value/particle number correction process according to the third embodiment executed by the controller in FIG. 2.

Each of FIGS. 8 and 9 shows a flowchart of an image analysis process in the image processing device 2A. The image analysis process shown in each of FIGS. 8 and 9 is executed by cooperation of the controller 21 and a program stored in the storage 25. FIG. 8 shows the flowchart related to a crosstalk removal process and FIG. 9 shows the flowchart related to a luminance value/particle number correction process.

The image analysis process according to the second embodiment includes a crosstalk removal process and a luminance value/particle number correction process. When the tissue slice is stained with a plurality of fluorescent substances having different fluorescent wavelengths, in the analysis targeting a bright spot of a specific color, signals of fluorescent substances of other colors leak, which is a phenomenon called crosstalk. An object of the crosstalk removal process in the present embodiment is to remove such a noise. The luminance value/particle number collection process in the present embodiment corrects the luminance value and the number of fluorescent dye accumulated particles for each fluorescent dye accumulated particle after removing the crosstalk.

In the following flowchart, multiple staining is performed to the tissue sample and the standard sample by using three types of immunostaining reagents respectively having fluorescent dye accumulated particles A, B and C having light emission wavelengths different from each other, and the control slide having each of the fluorescent dye accumulated particles A, B and C dispersed is provided. The color components of the fluorescent dye accumulated particles A, B and C are extractable by respective filters a, b and c.

In the following description, the fluorescent image obtained by image capturing of the fluorescent dye accumulated particle A with the filter a is referred to as a third fluorescent image Aa, the fluorescent image obtained by image capturing of the fluorescent dye accumulated particle A with the filter b is referred to as a third fluorescent image Ab, ..., the fluorescent image obtained by image capturing of the fluorescent dye accumulated particle C with the filter c is referred to as a third fluorescent image Cc. The average luminance value of fluorescent dye accumulated particle A in the third fluorescent image Aa is referred to as LAa, the average luminance value of fluorescent dye accumulated particle A in the third fluorescent image Ab is referred to as LAb, ..., average luminance value of fluorescent dye accumulated particle C in the third fluorescent image Cc is referred to as LCc.

When the crosstalk removal process in FIG. 8 is started, the first fluorescent image (step S801: input step) and the second fluorescent image (step S802) from the microscopic image acquiring device 1A are input by the communication interface 24. Then, nine types of third fluorescent images Aa, Ab, ..., Cc obtained by image capturing using filters a, b and c of the fluorescent dye accumulated particles A. B and C are input from the microscopic image acquiring device 1A by the communication interface 24 (step S803).

After the process of step S803, by the controller 21, the third bright spot region image extracting the bright spot region is created for all the third fluorescent images (step S804), and the third luminance integrated value of each bright spot region is calculated (step S805).

Next, by the controller 21, the average luminance value per fluorescent dye accumulated particle is calculated for each third fluorescent image on the basis of the distribution of third luminance integrated values (step S806: average luminance calculation step). That is, by the process of step S806, nine values of average luminance values LAa, LAb, ..., LCc are obtained.

Next, by the controller 21, the crosstalk correction coefficient is calculated on the basis of the ratio of average luminance value obtained by image capturing with different filters fora same fluorescent dye accumulated particle (step S807). In particular, the crosstalk correction coefficient can be represented by using determinant of three rows and three columns having components that are average luminance values LAa, LAb, ..., LCc.

After the process of step S807, by the controller 21, the noise leaking through filters not corresponding to the respective fluorescent dye accumulated particles A, B and C is removed for the first fluorescent image (step S808: crosstalk removal step). That is, by correcting the luminance value of the first fluorescent image using the crosstalk correction coefficient obtained in step S806, for example, the signal of fluorescent dye accumulated particle A leaking through the filter b can be removed.

Next, similarly to step S808, by the controller 21, the noise leaking through the filters not corresponding to the fluorescent dye accumulated particles A, B and C is removed for the second fluorescent image (step S809).

The crosstalk removal process is completed by the process of step S809, to proceed to the luminance value/particle number correction process shown in FIG. 9.

When the luminance value/particle number correction process in FIG. 9 is started and the first bright field image is inputted from the microscopic image acquiring device 1A by the communication interface 24 (Step S901), a first cell nucleus image in which a region of the cell nucleus is extracted from the first bright field image is created (Step S902).

Then, by the controller 21, a first bright spot region image is created from the first fluorescent image (Step S903). Next, a first luminance integrated value for each bright spot region of each of the fluorescent dye accumulated particles A, B and C in the first bright spot region image is calculated by the controller 21 (Step S904: luminance calculation step).

When the second bright field image is inputted from the microscopic image acquiring device 1A by the communication interface 24 (Step S905), a second cell nucleus image in which a region of the cell nucleus is extracted from the second bright field image is created by the controller 21 (Step S906).

Then, a second bright spot region image in which a bright spot region representing light emission of the fluorescent dye accumulated particle is extracted from the second fluorescent image is created by the controller 21 (Step S907). Next, a second luminance integrated value for each bright spot region in the second bright spot region image is calculated by the controller 21 (Step S908).

After the process of step S904 is finished, the number of fluorescent dye accumulated particles included in each bright spot region of each of the fluorescent dye accumulated particles A. B and C in the first bright spot region image is calculated from the average luminance values LAa, LBb and LCc per fluorescent dye accumulated particle and the first luminance integrated value of each bright spot region of each of the fluorescent dye accumulated particles A, B and C in the first bright spot region image by the controller 21 (step S909). That is, for the fluorescent dye accumulated particle A, for example, the particle number is calculated by using the average luminance value LAa of the third fluorescent image Aa obtained by image capturing through the filter a.

After the processes of steps S902 and S909 are finished, an addition process of the first cell nucleus image and the first bright spot region image is performed by the controller 21 (step S910), and the number of fluorescent dye accumulated particles per cell nucleus is calculated for each of the fluorescent dye accumulated particles A, B and C (step S911).

After the process of step S908 is finished, the number of fluorescent dye accumulated particles included in each bright spot region of each of the fluorescent dye accumulated particles A. B and C in the second bright spot region image is calculated by the controller 21 (step S912: tentative particle number calculation step).

After the processes of steps S906 and S912 are finished, an addition process of the second cell nucleus image and the second bright spot region image is performed by the controller 21 (step S913), and the number of fluorescent dye accumulated particles per cell nucleus is calculated for each of the fluorescent dye accumulated particles A, B and C (step S914).

The particle number correction coefficient is then calculated from the ratio between the reference number of fluorescent dye accumulated particles and the number of fluorescent dye accumulated particles per cell nucleus in the standard sample obtained in step S914 by the controller 21 (step S915). The reference number of fluorescent dye accumulated particles is set for each of the fluorescent dye accumulated particles A, B and C. That is, the particle number correction coefficient is calculated for each of the fluorescent dye accumulated particles A, B and C.

After the processes of steps S911 and S915 are finished, the number of fluorescent dye accumulated particles per cell nucleus calculated in step S911 is corrected for each of the fluorescent dye accumulated particles A. B and C by using the particle number correction coefficient calculated in step S915 by the controller 21 (step S916: particle number correction step). By the process of step S916, the number of fluorescent dye accumulated particles per cell nucleus is calculated for each of the fluorescent dye accumulated particles A, B and C, the number of fluorescent dye accumulated particles per cell nucleus being obtained by correcting the variation in the number of adhering to cell.

The luminance value correction process is completed by the process of step S916, and thus the image analysis process is finished.

The third embodiment of the present invention which has been described above includes a crosstalk removal step of removing crosstalk captured through filters not corresponding to the fluorescent dye accumulated particle by using the crosstalk correction coefficient calculated from a luminance ratio between a plurality of third fluorescent images obtained by image capturing using a plurality of respective filters with one fluorescent dye accumulated particle being dispersed without aggregating when staining is performed by using a plurality of types of fluorescent dye accumulated particles that have different light emission wavelengths and can be captured using a plurality of filters corresponding to respective light emission wavelengths. Accordingly it is possible to accurately perform quantitative analysis without being influenced by other fluorescent dye accumulated particles even when staining is performed with multiple colors.

In the third embodiment, the exposure time can be corrected on the basis of the third fluorescent image, similarly to the second embodiment.

Other Embodiments

The contents described in the above embodiments is a suitable example of the present invention, and the present invention is not limited thereto.

For example, in the above embodiments, the analysis is performed by using a region where the fluorescent dye accumulated particles exist as the bright spot portion and calculating the first luminance integrated value, second luminance integrated value and third luminance integrated value that are integrated values of luminance values of pixels included in the region. However, the present invention is not limited to this. For example, the analysis may be performed by using the pixel having a peak value of luminance value in the fluorescent bright spot as the bright spot portion. That is, the peak value can be detected from each fluorescent image as the first luminance value, second luminance value an third luminance value, and the average value of third luminance value in each bright spot region of third fluorescent image can be used as a unit luminance value.

In addition, in the above description, examples of using HDD, a semiconductor nonvolatile memory or the like as a computer readable medium for the program according to the present invention have been disclosed, but the medium is not limited to these examples. For other computer readable media, a portable recording medium such as CD-ROM can be applied. Moreover, as a medium that provides data of the program according to the present invention via a communication line, a carrier wave may be applied.

Besides, a detailed configuration and a detailed operation of each device constituting the pathological diagnosis support system 100 can also be appropriately modified within a range that does not depart from the scope of the present invention.

INDUSTRIAL APPLICABILITY

The present invention is applicable to a biological substance quantification method, an image processing device, a pathological diagnosis support system, and a program.

EXPLANATION OF REFERENCE NUMERALS 1A microscopic image acquiring device (image acquiring device)
2A image processing device
21 controller
22 operating unit
23 display
24 communication interface
25 storage
26 bus
3A cable
100 pathological diagnosis support system

The invention claimed is:
1. A biological substance quantification method of quantifying an expression amount of a specific biological substance in a target sample that is stained by using a fluorescent dye accumulated particle bondable to the specific biological substance, the method comprising:
  inputting a first fluorescent image obtained by image capturing of the target sample;
  luminance calculating comprising extracting a bright spot portion from the first fluorescent image and calculating a first luminance value which is a luminance value of the bright spot portion;
  particle number calculating comprising calculating a number of the fluorescent dye accumulated particle included in the bright spot portion extracted from the first fluorescent image by using the first luminance value, a second luminance value and a distribution of a third luminance value, the second luminance value being a luminance value of a bright spot portion extracted from a second fluorescent image obtained by image capturing of a standard sample for which an expression amount of the specific biological substance is measured in advance, and the third luminance value being a luminance value of each bright spot portion representing light emission of the fluorescent dye accumulated particle in a third fluorescent image obtained by image capturing of a preparation on which the fluorescent dye accumulated particle is dispersed without aggregating;

each of the bright spot portion is a region where the fluorescent dye accumulated particle exists, the first luminance value is a first luminance integrated value that is an integrated value of the luminance value of the bright spot portion extracted from the first fluorescent image, the second luminance value is a second luminance integrated value that is an integrated value of the luminance value of the bright spot portion extracted from the second fluorescent image, and the third luminance value is a third luminance integrated value that is an integrated value of the luminance value of the bright spot portion extracted from the third fluorescent image;

a unit luminance value calculating comprising calculating a unit luminance value per the fluorescent dye accumulated particle from the distribution of the third luminance integrated value adding up the luminance value of each of the bright spot portion representing the light emission of the fluorescent dye accumulated particle in the third fluorescent image;

a tentative particle number calculating comprising calculating a tentative number of the fluorescent dye accumulated particle included in the bright spot portion extracted from the first fluorescent image by using a first luminance integrated value and the unit luminance value; and a particle number correcting comprising correcting the tentative number of the fluorescent dye accumulated particle included in the bright spot portion extracted from the first fluorescent image by using the second luminance integrated value.

2. The biological substance quantification method according to claim 1, wherein the particle number calculating includes:

unit luminance value calculating comprising calculating a unit luminance value per the fluorescent dye accumulated particle from the distribution of the third luminance integrated value adding up the luminance value of each of the bright spot portion representing the light emission of the fluorescent dye accumulated particle in the third fluorescent image;

exposure time calculating comprising calculating an exposure time in the image capturing of each of the first fluorescent image and the second fluorescent image based on comparison between the unit luminance value and a reference luminance value per the fluorescent dye accumulated particle predicted under a predetermined condition;

tentative particle number comprising calculating a tentative number of the fluorescent dye accumulated particle included in the bright spot portion extracted from the first fluorescent image by using the first luminance integrated value and the reference luminance value; and particle number correcting comprising correcting the tentative number of the fluorescent dye accumulated particle included in the bright spot portion extracted from the first fluorescent image by using the second luminance integrated value, and each of the first fluorescent image and the second fluorescent image is an image taken with the exposure time calculated by the exposure time calculating.

3. The biological substance quantification method according to claim 1, wherein the particle number correcting is correcting using a particle number correction coefficient calculated from a ratio between a number of the fluorescent dye accumulated particle bonded to the bright spot portion in the second fluorescent image calculated by using the second luminance integrated value and a reference number of the fluorescent dye accumulated particle bonded to the bright spot portion predicted under a predetermined condition.

4. The biological substance quantification method according to claim 1, wherein the unit luminance value calculating calculates as the unit luminance value, a third luminance integrated value which is a mode among the third luminance integrated value.

5. The biological substance quantification method according to claim 1, comprising crosstalk removing comprising removing crosstalk by using a crosstalk correction coefficient calculated from a luminance ratio between a plurality of third fluorescent images each of which is the third fluorescent image, the third fluorescent images being captured with a plurality of respective filters by dispersing, without aggregating, one fluorescent dye accumulated particle which is the fluorescent dye accumulated particle, and the crosstalk being captured via a filter, among the filters, not corresponding to the one fluorescent dye accumulated particle, wherein the target sample is stained by using a plurality of types of fluorescent dye accumulated particles including the one fluorescent dye accumulated particle, the plurality of types of fluorescent dye accumulated particles having different light emission wavelengths and being capturable by using the filters corresponding to the respective light emission wavelengths.

6. An image processing device that quantifies an expression amount of a specific biological substance in a target sample which is stained by using a fluorescent dye accumulated particle bondable to the specific biological substance, the device comprising:

an inputter to input a first fluorescent image obtained by image capturing of the target sample; and a hardware processor that:

extracts a bright spot portion from the first fluorescent image and calculates a first luminance integrated value which is an integrated value of a luminance value of the bright spot portion; and calculates a number of the fluorescent dye accumulated particle included in the bright spot portion extracted from the first fluorescent image by using the first luminance integrated value, a second luminance integrated value and a distribution of a third luminance integrated value, the second luminance integrated value being an integrated value of a luminance value of a bright spot portion extracted from a second fluorescent image obtained by image capturing of a standard sample for which an expression amount of the specific biological substance is measured in advance, and the third luminance integrated value adding up a luminance value of each bright spot portion representing light emission of the fluorescent dye accumulated particle in a third fluorescent image obtained by image capturing of a preparation on which the fluorescent dye accumulated particle is dispersed without aggregating;

each of the bright spot portion is a region where the fluorescent dye accumulated particle exists, the first luminance value is a first luminance integrated value that is an integrated value of the luminance value of the bright spot portion extracted from the first fluorescent image, the second luminance value is a second luminance integrated value that is an integrated value of the luminance value of the bright spot portion extracted from the second fluorescent image, and the third luminance value is a third luminance integrated value that is an integrated value of the luminance value of the bright spot portion extracted from the third fluorescent image;

a unit luminance value calculating comprising calculating a unit luminance value per the fluorescent dye accumulated particle from the distribution of the third luminance integrated value adding up the luminance value of each of the bright spot portion representing the light emission of the fluorescent dye accumulated particle in the third fluorescent image;

a tentative particle number calculating comprising calculating a tentative number of the fluorescent dye accumulated particle included in the bright spot portion extracted from the first fluorescent image by using a first luminance integrated value and the unit luminance value; and a particle number correcting comprising correcting the tentative number of the fluorescent dye accumulated particle included in the bright spot portion extracted from the first fluorescent image by using the second luminance integrated value.

7. A non-transitory recording medium storing a computer readable program causing a computer that quantifies an expression amount of a specific biological substance in a target sample which is stained by using a fluorescent dye accumulated particle bondable to the specific biological substance to perform:

inputting that is inputting a first fluorescent image obtained by image capturing of the target sample;

luminance calculating that is extracting a bright spot portion from the first fluorescent image and calculating a first luminance integrated value which is an integrated value of a luminance value of the bright spot portion; and particle number calculating that is calculating a number of the fluorescent dye accumulated particle included in the bright spot portion extracted from the first fluorescent image by using the first luminance integrated value, a second luminance integrated value and a distribution of a third luminance integrated value, the second luminance integrated value being an integrated value of a luminance value of a bright spot portion extracted from a second fluorescent image obtained by image capturing of a standard sample for which an expression amount of the specific biological substance is measured in advance, and the third luminance integrated value adding up a luminance value of each bright spot portion representing light emission of the fluorescent dye accumulated particle in a third fluorescent image obtained by image capturing of a preparation on which the fluorescent dye accumulated particle is dispersed without aggregating; and each of the bright spot portion is a region where the fluorescent dye accumulated particle exists, the first luminance value is a first luminance integrated value that is an integrated value of the luminance value of the bright spot portion extracted from the first fluorescent image, the second luminance value is a second luminance integrated value that is an integrated value of the luminance value of the bright spot portion extracted from the second fluorescent image, and the third luminance value is a third luminance integrated value that is an integrated value of the luminance value of the bright spot portion extracted from the third fluorescent image;

a unit luminance value calculating comprising calculating a unit luminance value per the fluorescent dye accumulated particle from the distribution of the third luminance integrated value adding up the luminance value of each of the bright spot portion representing the light emission of the fluorescent dye accumulated particle in the third fluorescent image;

a tentative particle number calculating comprising calculating a tentative number of the fluorescent dye accumulated particle included in the bright spot portion extracted from the first fluorescent image by using a first luminance integrated value and the unit luminance value; and a particle number correcting comprising correcting the tentative number of the fluorescent dye accumulated particle included in the bright spot portion extracted from the first fluorescent image by using the second luminance integrated value.

8. A pathological diagnosis support system, comprising: the image processing device according to claim 6; and an image acquiring device that acquires the first fluorescent image, the second fluorescent image and the third fluorescent image.

9. The biological substance quantification method according to claim 2, wherein the particle number correcting is correcting using a particle number correction coefficient calculated from a ratio between a number of the fluorescent dye accumulated particle bonded to the bright spot portion in the second fluorescent image calculated by using the second luminance integrated value and a reference number of the fluorescent dye accumulated particle bonded to the bright spot portion predicted under a predetermined condition.

10. The biological substance quantification method according to claim 2, wherein the unit luminance value calculating is calculating, as the unit luminance value, a third luminance integrated value which is a mode among the third luminance integrated value.

* * * * *